United States Patent [19]

Gilbert et al.

[11] Patent Number: 6,004,510
[45] Date of Patent: Dec. 21, 1999

[54] ARTICLES, COMPOSITIONS AND PROCESS FOR CLEANING SURFACES BY USE OF A CATALYST AT THE SURFACE

[75] Inventors: Peter Gilbert, Hale Barnes; Martin Vincent Jones, Neston, both of United Kingdom

[73] Assignee: Lever Brothers Company, New York, N.Y.

[21] Appl. No.: 08/875,783

[22] PCT Filed: Jan. 31, 1996

[86] PCT No.: PCT/EP96/00443

§ 371 Date: Aug. 5, 1997

§ 102(e) Date: Aug. 5, 1997

[87] PCT Pub. No.: WO96/24385

PCT Pub. Date: Aug. 15, 1996

[30] Foreign Application Priority Data

Feb. 9, 1995 [GB] United Kingdom .................. 9502493

[51] Int. Cl.$^6$ ........................................ A61L 9/00
[52] U.S. Cl. ................ 422/29; 422/28; 422/34; 422/37; 424/405; 514/840
[58] Field of Search ................ 422/28, 29, 34, 422/37; 134/901; 424/429, 405; 514/839, 840; 351/160 R

[56] References Cited

U.S. PATENT DOCUMENTS 4,826,658   5/1989  Kay ............................................ 422/30
5,077,258  12/1991  Phillips et al. ............................ 422/30
5,213,801   5/1993  Sakuma et al. ........................... 424/429
5,246,662   9/1993  Ripley et al. ............................. 422/29
5,270,002  12/1993  Neff, II et al. ............................ 422/30
5,275,784   1/1994  Perlaky ..................................... 422/30
5,340,583   8/1994  Dziabo et al. ........................... 424/412
5,468,448  11/1995  Nicolson et al. ......................... 422/30
5,515,117   5/1996  Dziabo et al. ...................... 351/160 H
5,556,480   9/1996  Rontome et al. ......................... 422/30

*Primary Examiner*—Krisanne Thornton
*Attorney, Agent, or Firm*—Neal Y. Gilbert, Esq.

[57] ABSTRACT

The disclosure relates to a process for the treatment of a surface with a hygiene agent which can include the steps of: a) providing at the surface a non-photochemical catalyst (such as a transition metal compound) which catalyses the formation of the hygiene agent from one or more precursors, whereby the catalyst becomes deposited at the surface, and, b) subsequently treating the surface with a treatment agent (such as a solution of hydrogen peroxide) having the or each hygiene agent precursor, such that the hygiene agent is generated at the surface. The disclosure also provides a process which includes the step of treating the surface which has a non-photochemical catalyst bound thereto with a treatment agent having at least one hygiene agent precursor which forms said hygiene agent in the presence of the catalyst and, a process for the manufacture of an article which includes the step of incorporating therein, at the time of manufacture, a non-photochemical catalyst capable of transforming at least one hygiene agent precursor into a hygiene agent.

11 Claims, 4 Drawing Sheets

ARTICLES, COMPOSITIONS AND PROCESS FOR CLEANING SURFACES BY USE OF A CATALYST AT THE SURFACE

TECHNICAL FIELD

The present invention relates to articles and a process for treatment of surfaces of said articles, particularly when said articles have been contaminated with microorganisms and to compositions for treatment of articles. More particularly, the invention relates to a process which facilitates the reduction of elimination of contamination by microorganisms through the application of hygiene agents or precursors thereof.

BACKGROUND OF THE INVENTION

Contamination of surfaces with microorganisms can cause problems in a number of areas. For example, microorganisms which are injurious to health may be present on a surface on which food is prepared. If these organisms are transferred to the food, illness can result for a person who consumes the food. Further problems are caused by microbial contamination of the inner walls of air-conditioning ducts or water supply pipes within buildings, or by contamination of devices for use in or on the human body, for example, contact lenses, surgical instruments etc. These problems not only include the risks to health but also, especially in the case of pipes and the like, increased fluid frictional resistance, increased heat transfer resistance and biocorrosion. Many other examples are apparent from the literature and could be cited.

Many compositions are known and used for the cleaning and disinfection of surfaces. Almost all these compositions share the common feature that they contain a hygiene agent which is toxic to or inhibits the growth of microorganisms. Typical hygiene agents include, strong acids, alkali's, phenolics, oxidising agents such as peracids and hypohalides and charged species such as cationic surfactants. These are generally highly reactive species which exhibit this reactivity in terms of one or more of, short shelf life, toxic, corrosive and irritant properties and, in general, these components are required at relatively high levels in formulations to obtain a satisfactory result.

In many circumstances microorganisms will grow on a surface to form a confluent or part-confluent biofilm. Bacterial biofilms are regarded as problematic in household and industrial hygiene as well as in medicine where they can act as reservoirs for spoilage organisms or pathogens or can lead to so-called biofouling. Biofilms are regarded as problematic in infections associated with indwelling medical devices and other articles in contact with wet body tissues, such as contact lenses.

Conventional approaches to the control of biofilms, such as the application of the hygiene agents described above have demonstrated that these films are recalcitrant. A number of factors are thought to contribute to this recalcitrance, and it is believed that a major factor is the ability of the glycocalyx, an extracellular polymer of polysaccharides and glycoproteins to react with highly reactive species, such as the above mentioned oxidising agents or halogens and to bind the above mentioned charged species. It is believed that these interactions prevent effective access of the hygiene agent beyond the exposed surface of the biofilm.

It is known that the activity of certain hygiene agents can be improved by addition of other components. For example, the reaction of hypochlorite solutions with strong acids will produce chlorine a potent, if somewhat dangerous, hygiene agent. It is also known to generate hygiene agents by catalytic action. EP 0436466 discloses a method of disinfecting a hydrogen peroxide stable material by contacting said material with a hydrogen peroxide containing solution and a hydrogen peroxide decomposition means such as a catalyst on a separate support.

WO 93/00815 discloses how it is possible to bind a photosensitiser to a surface which is capable of catalysing the formation of singlet oxygen from triplet oxygen under the influence of visible light, thereby providing photobacterial properties and an autosterile character to the surface upon exposure to visible light. Compositions for use in such a method comprise 0.1–1.0% by weight of the photosensitiser, which may be a porphyrin or phthalocyanine, preferably in the unmetalled form. Salts of the meso-tetra(N-octyl-4-pyridinium)porphyrin tetracation are known to have both cytotoxic and phocytotoxic properties. Similar techniques are known for the preparation of ceramic tiles and other such sanitary ware. In such systems, as disclosed in the trade literature of Toto Ltd of Minato-Ku, Tokyo, photoactivation of a compound based on titanium dioxide is believed to produce an excited species which is effective as a hygiene agent.

A disadvantage of the photochemical systems is that they are less effective or ineffective under low light conditions or in the dark. Given that many of situations in which microbial contamination can occur are not well lit (such as the inside of air-conditioning ducts or water supply pipes) there is a need to provide hygiene systems which are effective against biofilms, both in lit and dark conditions without requiring the use of high levels of reactive hygiene agents.

BRIEF DESCRIPTION OF THE INVENTION

We have determined that the efficacy of hygiene agents can be much improved if the hygiene agent is generated non-photochemically from a precursor compound at a surface contaminated with a biofilm rather than being prepared separately and applied to the exposed surface of the biofilm. This may be accomplished by activating the surface with a dark-acting catalyst prior to the growth of a biofilm and subsequent treatment of the contaminated surface with a substrate for the catalyst which is transformed by the catalyst into a hygiene agent.

Without wishing to limit the invention by reference to a theory of operation, it is believed that the production of the hygiene agent at the surface produces a concentration gradient which diminishes away from the contaminated surface, rather than towards the surface as is the case when the agent is applied to the exposed surface of the biofilm. Moreover, consumption of the or each hygiene agent precursor at the contaminated surface establishes a concentration gradient of said precursors which promotes diffusion of said precursors towards the contaminated surface.

Accordingly, a first aspect of the present invention provides a process for the disinfection of a surface with a hygiene agent which comprises the steps of:

a) providing at the surface a non-photochemical catalyst which catalyses the formation of the hygiene agent from one or more precursors, whereby said catalyst become deposited at said surface, and, b) subsequently treating the surface with a treatment agent comprising the or each hygiene agent precursor, such that the hygiene agent is generated at and disinfects said surface.

It should be noted that for certain catalysts it is not necessary that the above-mentioned step (a) be performed before every peformance of step (b) as in these embodiments there will be sufficient catalyst remaining from previous cleaning cycles to produce the hygiene agent from the or each precursor: thus an important aspect of the present invention is that the process can consist of a small number of treatments to provide the catalyst at the surface and a larger number of subsequent treatments to supply the catalyst with its substrate. Thus the deposited catalyst can be used for a single disinfection operation or a plurality of such operations.

The term 'non-photochemical' as used in this specification does not exclude the possibility that the properties of the catalyst will be modified by illumination, but it is essential that the catalyst is capable of generating the hygiene agent substantially in the absence of light. Thus the invention has the important advantage that it enables the catalytic generation of hygiene agents in dark and generally inaccessible places such as the interiors of pipes and ducts without the requirement of illumination of these places.

Accordingly, a second aspect of the present invention provides a process for the disinfection of a surface having microbial growth thereupon which comprises the step of treating the surface which has a non-photochemical catalyst bound thereto with a treatment agent comprising at least one hygiene agent precursor which forms said hygiene agent in the presence of said catalyst.

It should be noted that catalyst can be deposited at the surface by incorporation of catalytic material into the material from which the surface is formed prior to the formation of the surface.

Accordingly, a fourth aspect of the present invention relates to a process for the manufacture of a three-dimensional article which includes the step of incorporating therein, at the time of manufacture, a non-photochemical catalyst capable of transforming at least one hygiene agent precursor into an hygiene agent effective against microorganisms, wherein the article is such that in use microbial growth will occur on a surface of the article.

A fifth aspect of the invention relates to a three-dimensional article having incorporated therein, at the time of manufacture, a non-photochemical catalyst capable of transforming at least one hygiene agent precursor into an hygiene agent, wherein the article is such that in use microbial growth will occur on a surface of the article.

DETAILED DESCRIPTION OF THE INVENTION

Figure 1:
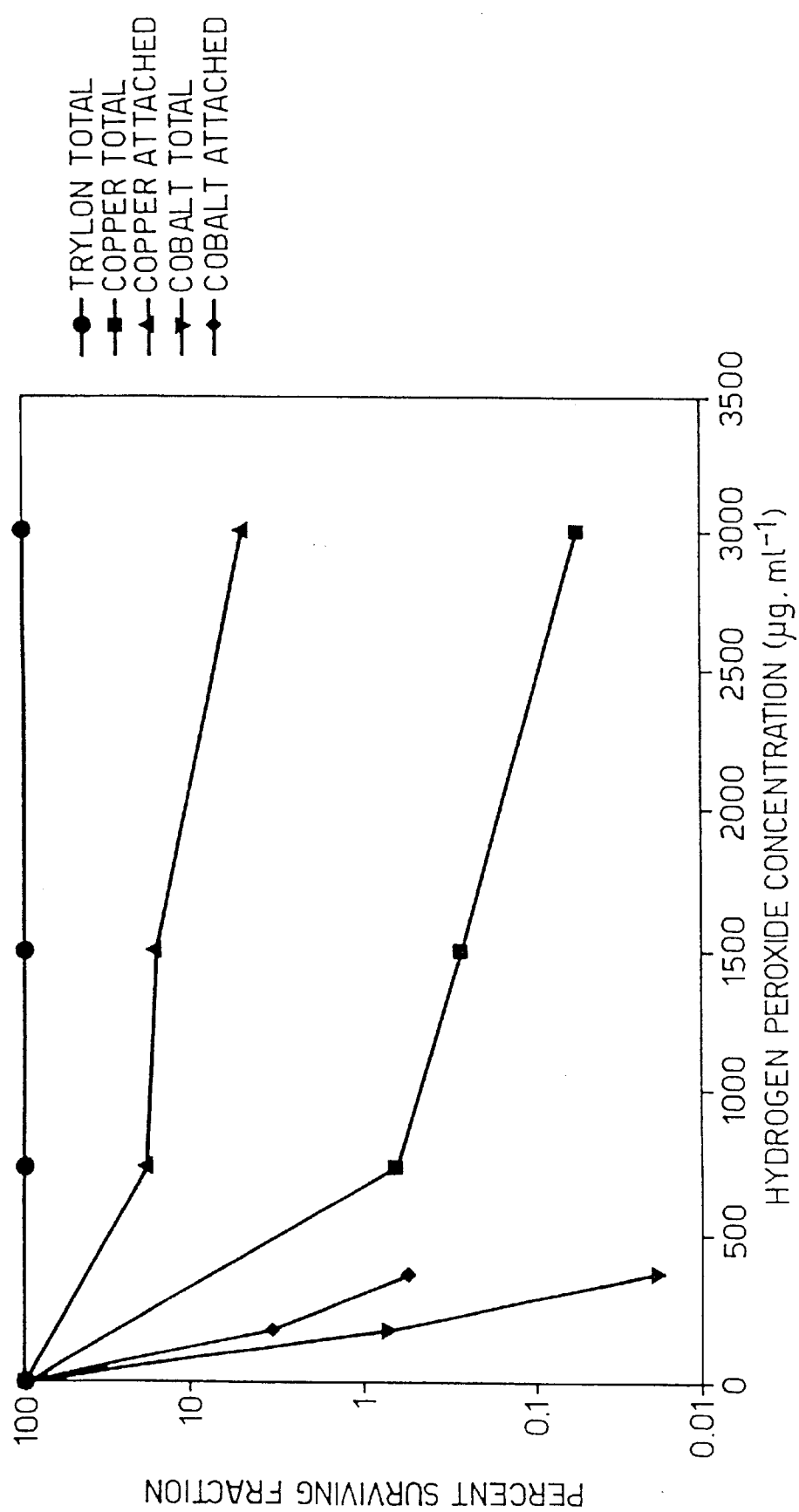
FIG. 1 is a plot of hydrogen peroxide concentration vs. percentage surviving fraction of microorganisms (both total and attached).

It is an essential feature of the present invention that the hygiene agent is formed by treatment of the catalyst with the or each precursor for a hygiene agent. In certain embodiments of the present invention, these precursors themselves have anti-bacterial or other anti-microbial properties. These properties may be exhibited to a lesser or greater extent than those of the hygiene agent. In other embodiments the precursors have is substantially no antimicrobial properties and, it is preferable that, to the advantage of the user, they exhibit none or significantly less of the toxic, corrosive and/or irritant properties mentioned above.

Hygiene Agents and Catalysts

As mentioned above the treatment agent contains at least one hygiene agent precursor which forms said hygiene agent in the presence of said catalyst. In the context of the present invention the term hygiene agent includes both biocidal and non-biocidal species. While it is preferable that the hygiene agents are biocidal it is also envisaged that the hygiene agents can function in a more general sense by physical removal of at least a part of the microbes from the surface for example by weakening the attachment of the microbes to the surface or by the generation of gas bubbles at the surface. Thus in certain embodiments of the invention the hygiene agent is effective against micro-organisms by virtue of physical rather than chemical effects.

Suitable hygiene agent precursors include peroxy compounds, isothiazolones, halides and hypohalites. It is preferable that these precursors are presented as a liquid composition and it is particular preferred that said liquid composition should be essentially free of the catalyst.

Suitable peroxy compounds include, hydrogen peroxide, sodium peroxide, peracetic acid, performic acid and mono-persulphate salts. In addition to the above-mentioned acids the use of imidoperoxy--carboxylic acids including e-N-N-phthaloyl-amino-peroxy-caproic acid is envisaged. Other peroxy-carboxylic acids, are known from a publication entitled "TAED and new peroxycarboxylic acids as highly efficient bleach Systems", 80th AOCS Meeting, Cincinnati Ohio, May 1989 and are incorporated herein by reference. Hydrogen peroxide and potassium monpersulphate are particularly preferred as the peroxy compounds.

Suitable catalysts for the decomposition of peroxy compounds include transition metals and compounds thereof. It is preferred to use compounds of the transition metals rather than the metals per se. Preferred transition metals are cobalt, copper, platinum, titanium, manganese, vanadium, silver, zinc, palladium, iridium and iron. Particularly preferred catalysts include cobalt, manganese and copper compounds, more particularly manganese dioxide and copper or cobalt phthalocyanine. These and other catalysts can be applied by treating the surface with a composition containing the catalyst so as to deposit said catalyst on the surface.

We have found that the combination of cobalt phthalocyanine as the catalyst and potassium monopersulphate as the hygiene agent is particularly effective in reducing the viable cell count of biofilm populations when said biofilms are grown on plastics materials comprising cobalt phthalocyanine and subsequently treated with a solution containing potassium mono-persulphate.

The preparation of stable solutions of peroxy-compounds and hypohalites is well documented in the art. It is known that these solutions should preferably be free of the above-mentioned metals as these are known to significantly reduce the shelf life of the solutions. We have found that the provision of the catalyst at the surface to be disinfected enables effective results to be obtained with very low concentrations of the treatment agent and significantly lower levels than would be required without the use of the catalyst. Thus, for example, in the case where the treatment agent comprises hydrogen peroxide and the catalyst comprises a transition metal, we have established that substantial removal of biofilm may be achieved using hydrogen peroxide concentrations of less than 3 mg/ml. Such concentrations were totally ineffective for removing and disinfecting similar biofilms from surfaces not provided with a catalyst. It is therefore a significant advantage of the invention that lower concentrations of the precursor may be used, particularly, for example, in surgical or medical applications.

The invention is not limited to the use of such low levels of hygiene agent precursor in the treatment agent since, in some circumstances, the use of higher levels may be necessary or desirable. Generally, the concentration of the hygiene agent precursor will be from 10 ppm to 40% w/v.

Alternative catalysts include enzymes. Particularly preferred are enzymes of the 'oxidase' class which produce hydrogen peroxide when exposed to a suitable substrate.

One class of enzymes envisaged for use in the present invention are the glucose oxidases, although it is envisaged that other enzymes such as the haloperoxidases could also be used.

The process of the invention is particularly useful when applied to ceramic, glass and other such hard surfaces and, in particular, to plastics and other polymeric materials (including kitchen laminates) which, unlike certain metals, do not have the inherent ability to catalyse the conversion of precursors to hygiene agents. While the invention is generally described herein with reference to general household and industrial surface cleaning the application of the process of the invention to specialist cleaning tasks such as the cleaning and sterilisation of medical appliances including contact lenses and dentures, or medical or personal care apparatus including toothbrushes is not intended to be excluded.

As noted above, in certain embodiments of the invention it is envisaged that the catalyst is incorporated into articles or applied to the surface thereof in the process of manufacture of the articles. It is preferable that the surface as manufactured incorporates the catalyst. Accordingly the present invention extends to many articles of laboratory and household equipment including pipes and tubes, racks and containers, tools and utensils, including wipes.

Preferred articles are manufactured of a plastics material which has the catalyst distiributed therein. Alternatively, the catalyst can be applied to the surface of the article in the form of a coating.

It is particularly preferred that the treatment agent is a liquid which comprises an aqueous carrier and one or more precursors of the or each hygiene agent in solution. It is preferred that the one or more precursors of the or each hygiene agent forms a stable solution or suspension at a level of up to 1% in water, i.e. gaseous precursors are generally avoided and solid or liquid precursors are preferred. The liquid precursors can be in the form of mists, sprays and aerosols. One gaseous hygiene agent which is envisaged as useful in the practice of the present invention is hydrogen peroxidse in a vapourised form. This vapour is believed to be highly reactive and to require special precautions to be taken when it is used at conventional concentrations. It is believed that the present invention provides for the use of effective levels of hydrogen peroxide vapour which are lower than the conventional concentrations. Similarly, it is believed that organic acids in vapour form can be employed.

Surfactants

It is preferred that the treatment agent further comprises a surfactant. Surfactants can be nonionic, anionic, cationic, amphoteric or zwitterionic provided that they, and where appropriate their counter-ions, do not react substantially with the hygiene agent or its precursor.

Suitable nonionic detergent active compounds can be broadly described as compounds produced by the condensation of alkylene oxide groups, which are hydrophilic in nature, with an organic hydrophobic compound which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Particular examples include the condensation product of aliphatic alcohols having from 8 to 22 carbon atoms in either straight or branched chain configuration with ethylene oxide, such as a coconut oil ethylene oxide condensate having from 3 to 10 moles of ethylene oxide per mole of coconut alcohol; condensates of alkylphenols whose alkyl group contains from 6 to 12 carbon atoms with 3 to 10 moles of ethylene oxide per mole of alkylphenol.

The preferred alkoxylated alcohol nonionic surfactants are ethoxylated alcohols having a chain length of C9–C11 and an EO value of at least 3 but less than 10. Particularly preferred nonionic surfactants include the condensation products of $C_{10}$ alcohols with 3–8 moles of ethylene oxide. The preferred ethoxylated alcohols have a calculated HLB of 10–16. An example of a suitable surfactant is 'IMBENTIN 91-35 OFA' (TM, ex. Kolb AG) a $C_{9-11}$ alcohol with five moles of ethoxylation.

When present, the amount of nonionic detergent active to be employed in the composition of the invention will generally be from 0.1 to 30% wt, preferably from 1 to 20% wt, and most preferably from 3 to 10% wt for non-concentrated products. Concentrated products will have 10–20% wt nonionic surfactant present, whereas dilute products suitable for spraying will have 0.1–5% wt nonionic surfactant present.

Minors and Optional Components

The composition according to the invention can contain other minor, inessential ingredients which aid in their cleaning performance and maintain the physical and chemical stability of the product. Typically, these will be materials known in the art of formulation of cleaning compositions.

For example, the composition can contain detergent builders. In general, the builder, when employed, preferably will form from 0.1 to 25% by weight of the composition.

Optionally, the composition can include one or more amphoteric surfactants, preferably betaines, or other surfactants such as amine-oxide and alkyl-amino-glycinates. Betaines are preferred for reasons of cost, low toxicity (especially as compared to amine-oxide) and wide availability. These components should be selected such that they do not react with the hygiene agent precusor or other components of the product.

Metal ion sequestrants, including ethylenediamine-tetraacetates, aminopolyphosphonates (such as those in the $DEQUEST^R$ range) and phosphates and a wide variety of other poly-functional organic acids and salts, can also optionally be employed. Again, these components should be selected such that they do not react with the hygiene agent precusor or other components of the product.

Hydrotropes, are useful optional components. Suitable hydrotropes include, alkali metal toluene sulphonates, urea, alkali metal xylene and cumene sulphonates, polyglycols, >20EO ethoxylated alcohols, short chain, preferably $C_2$–$C_5$ alcohols and glycols. Preferred amongst these hydrotropes are the sulphonates, particularly the cumene, xylene and toluene sulphonates. Again, these components should be selected such that they do not react with the hygiene agent precusor or other components of the product.

Typical levels of hydrotrope range from 0–5% for the sulphonates. Correspondingly higher levels of urea and alcohols are required. Hydrotropes are not always required for dilute, sprayable products, but may be required if lower EO or longer alkyl ethoxylates are used or the cloud point needs to be raised considerably. The cumene sulphonate is the most preferred hydrotrope.

Compositions according to the invention can also contain, in addition to the ingredients already mentioned, various other optional ingredients such as, solvents, colourants, optical brighteners, soil suspending agents, detersive enzymes, compatible bleaching agents, gel-control agents, freeze-thaw stabilisers, further bactericides and or antimicrobials, perfumes and opacifiers. It is also envisaged that the compositions according to the invention can be delivered in an encapsulated form such that there is a time-delayed release of either the catalyst or the treatment agent at the surface.

A number of non-limiting applications in which it is envisaged that the invention can be used are given below:
a) Industrial, institutional and domestic cleaning and/or disinfection of hard surfaces to which the catalyst is applied including metal, plastics materials or other polymers, ceramic, and glass surfaces used for the preparation of food and beverages (e.g. worktops, conveyor systems and utensils) or other industrial, institutional and domestic surfaces such as sanitary ware.
b) Industrial, institutional and domestic fluid supply applications, e.g. provision of the catalyst on the inner wall of a pipe (e.g as plastics pipe) used for supplying drinking water, or the inner wall of an air conditioning duct, or the inner wall of an oil pipeline. Further applications of this category include provision of the catalyst in heat exchangers and radiators so as to permit disinfection thereof and prevent biofouling. In these instances disinfection is effected by flowing the treatment agent through the installation concerned.
c) Applications in disinfection of medical, surgical or dental apparatus, equipment, facilities or supplies e.g. provision of the catalyst on a surface of a catheter, contact lens, surgical dressing or surgical instrument (e.g. an endoscope) so as to permit ready disinfection thereof.
d) Applications in coating technology, e.g. by incorporation of the catalyst in a paint varnish or other coating composition to be applied to a surface so that the surface can be subsequently disinfected.
e) Horticultural applications, e.g. for sterlising the surfaces of greenhouses using low concentrations of the precursor material.
f) Marine applications to treat biofouling of submersed portions of vessels or structures.
g) Soft surfaces including fabrics (eg. in dressings, wipes and cloths), and non-living materials of biological origin (such as wood).
h) Applications relating to personal washing of skin and hair and personal oral care processes and articles, including tooth-brushes.

In order that the invention may be further understood it will be described hereinafter with reference to the following illustrative examples:

EXAMPLES

Example 1

Use of manganese dioxide catalyst in surface treatment

Sufficient polystyrene foam was dissolved in a small quantity of chloroform to provide a thin solvent-based cement. Into this cement was mixed a minor amount of manganese dioxide. The resulting product was applied to glass cover-slips and allowed to dry. In a similar manner, glass cover slips were partially coated with an identical cement composition which did not contain the manganese compound.

After the chloroform had evaporated, both sets of slips were immersed in a Luria broth culture of *E. coli* (approximately $10^7$ cells/ml. The broth was maintained in a heated waterbath so as to allow a biofilm to become established on the surface of the coverslips. Typical biofilms produced in this manner have a cell density of around $10^6$ cells/cm$^2$.

After the biofilm had been produced, the coverslips were removed from the broth and treated with solutions of hydrogen peroxide. It was noted, by inspection, that this process removed significantly more of the biofilm from the slip to which the manganese dioxide containing cement had been applied, as compared with the slips which had simply been coated with the cement. It was also noted that the production of oxygen by the decomposition of hydrogen assisted in the removal of the biofilm from the surface.

Example 2

Use of copper and cobalt phthalocyanin catalysts in manufacture.

Trylon (TM) Resin (polyester resin in styrene monomer, ex. Trylon Ltd, Wollaston, Northants, UK) was mixed with Trylon (TM) Hardener (methyl ethyl ketone peroxide) at a hardner concentration of about 1%, poured in 50 ml boiling tubes and allowed to harden overnight at room temperature. Rods of plastics material were extracted by breaking the tubes.

Copper phthalocyanine (ex Sigma.) was incorporated into certain batches of the plastics material by adding ground catalyst to 1 ml of the resin, mixing and adding the balance of the components to obtain a plastics material comprising 100 micrograms/liter of the catalyst. Similar experiments were performed with cobalt phthalocyanine.

Disks of plastics material 1 mm thick and 20 mm in diameter were cut from the rods. Prior to use all disks were either placed in media and autoclaved at 121 Celcius for 20 minutes to sterilise both disks and media, or sterilised by storage in ethanol (70% wt vol).

The effect of the presence of the catalyst was evaluated by the effect on biofilms obtained from a stable, mucoid, clinical isolate of *Pseudomonas aerucinosa* PaWH. Cultures were maintained on Tryptone Aoya Agar (TSA, Oxoid (TM) CM131) slants, in the dark, at 4 Celcius, after overnight incupation at 37 Celcius.

Where required, overnight cultures were prepared from the slopes by inoculating 100 ml volumes of Tryptone Soya Broth (TSB, Oxoid CM129), contained in 250 ml Erlenmeyer flasks, and incubating at 37 Celcius for 16 h in an orbital incubator (200 rpm). 20 ml volumes of sterile saline containing a range of $H_2O_2$ concentrations (0 to 3.75 mg.ml-1) were inoculated with an overnight culture of *Ps. aeruginosa* in such a manner that a final concentration of $10^8$ colony forming units (c.f.u) per ml was obtained. Test suspensions were left at room temperature for 30 minutes. After exposure, the suspensions were serially diluted to neutralise the biocide and 5 replicates were plated out for each dilution, to determine numbers of surviving cells.

Trylon discs with or without catalyst incorporated within them were clamped vertically within a cassette made out of Teflon. The cassette holds up to 16 discs in a radial arrangement. When immersed in culture medium (200 ml) and contained within a 500 ml beaker, the cassette allowed the free circulation of liquid to the discs. Beakers (500 ml) containing TSB (200 ml) and empty cassettes were sterilised by autoclaving and sterile discs were then added aseptically. Attachment of microorganisms was initiated by inoculation of the growth medium with a colony taken from a Tryptone Soya Agar plate. The device was incubated in a shaking incubator (37° C., 200 rpm) for 24 hours.

Discs, with their associated biofilms (above) were removed from the cassette, rinsed in two successive volumes (20 ml) of sterile saline (to remove loosely associated cells) and immersed in biocide (20 ml) for 30 minutes at room temperature. After exposure the discs were rinsed in two successive volumes (20 ml) of sterile saline (rinse n°1), and transferred to a sample tube containing 10 ml sterile saline. Sodium thiosulphate at 3.75 mg/ml was employed instead of sterile saline when the hygiene agent precursor was KMPS.

The tubes were then shaken vigorously for 10 minutes in a flask shaker (Griffin and George Scientific, London, UK) in order to remove the majority of the biofilm cells. It is thought that this process removes those cells that are attached only to other cells, while leaving those that are firmly attached to the test surface. The rinses and vigorous shaking in diluent of the biofilms serves to further neutralise (where required) and stop the action of the biocide. Discs were removed and further rinsed in three successive 20 ml volumes of sterile saline (rinse n°2). Finally, the discs were transferred to a succession of 15 TSA plates. These plates were incubated and viable counts made. Viable counts were also performed on both rinse solutions, on the shake solution, and the residual solution from the biocide treatment vial. These viable counts were combined to give an estimate of the surviving population that could be rinsed-off and/or removed from the biofilm by shaking after treatment. The results from the plate succession indicate not only the numbers of viable cells remaining firmly in association with the test surface, but also the ease with which they can be removed by friction.

Colonies associated with the plate succesisions arose from cells which had resisted removal either by rinsing or vigorous shaking in saline. Accordingly, results were divided into two categories: (1) effect of biocide on attached biofilm populations, derived from the numbers of c.f.u. transferred, from three replicate discs, to each succession of 15 TSA plates, and (2) effect of biocide on total biofilm populations, expressed as the sum of attached populations and of those organisms removed during rinsing and shaking after exposure to biocide.

After estimation of the number of surviving cells by the plate succession method the mean c.f.u. decreased exponentially with plate succession number. Regression analysis was performed using an SPSS statistics package, and lines of best fit determined. Data was fitted to equation 1:

$$CFU = A \cdot 10^{-KN} \quad \{1\}$$

where:

CFU is the number of organisms transferred to any given TSA plate,

A is a constant corresponding to the intercept value of the best fit line with the ordinates axis, K is the reduction exponent of the best fit line, and is believed to give a measure of the strength of attachment to the surface, N is the plate succession number From equation 1, and with known A and K values, it was possible to calculate the total number of organisms on each disc.

Similar experiment were performed with potassium monopersulphate as an alternative to the hydrogen peroxide biocide.

Table 1 below gives the concentration of biocide in micrograms/ml required to reduce by 90% the numbers of viable cells recovered from attached biofilms on Trylon disks containing either copper or cobalt phthalocyanine as determined by the above described agar succession method, when exposed to hydrogen peroxide and potassium monopersulfate (KMPS).

TABLE 1

|  | $H_2O_2$ | KMPS |
|---|---|---|
| Cu-catalyst | 2200 | 374 |
| Co-catalyst | 150 | 5 |

Table 1 shows that KMPS was generally more effective against attached biofilm populations on catalyst containing disks than was hydrogen peroxide and that the KMPS/cobalt phthalocyanine combination was the most effective of the combinations tested.

Table 2 below gives the concentration of biocide in micrograms/ml required to reduce by 90% the numbers of viable cells recovered from total biofilm populations and, where specified, plantonic populations on Trylon disks containing either copper or cobalt phthalocyanine, when exposed to hydrogen peroxide and potassium permonosulphate.

TABLE 2

|  | $H_2O_2$ | KMPS |
|---|---|---|
| Cu-catalyst | 375 | 200 |
| Co-catalyst | 125 | 3.75 |
| Planktonic | 1125 | 1200 |

From the results in Table 2 it can be seen that KMPS appears to be significantly more affective against the total biofilm population than hydrogen peroxide. The KMPS/cobalt phthalocyanine combination achieved 90% reduction in viable cells at concentrations of up to 100 times lower than for other combinations.

We have determined that, at a concentration of 3 mg.ml-1, there is a 1.5 log cycle decrease in the percentage survival of biofilm cells attached to cobalt phthalocyanine containing discs whereas those cells grown and treated with hydrogen peroxide on Trylon alone displayed no measurable decrease in viability. It was also noted that hydrogen peroxide treatment increased the value of the blot succession reduction exponent demonstrating that, not only was there an increase in hydrogen peroxide-mediated killing, but also that those cells surviving exposure to hydrogen peroxide were more loosely attached to the surface and as a result more easily removed.

The plate succession method enables the effects of the biocide on the complete original biofilm population to be estimated, by addition of the CFU obtained to the estimated residual attached population. Viability of total biofilms decreased to a much greater extent (3 log cycles) than that of the residual attached populations and, at a concentration of 3 mg.ml-1 hydrogen peroxide, to the same extent as that of planktonic populations. This can be explained by the fact that cells removed during rinse and shake steps are those cells that are more loosely attached to the substratum, or bound only to other cells. These cells do not necessarily benefit from the protection afforded by biofilm mode of growth per se (altered physiology, encasement within a matrix of extracellular polymeric substance (EPS) hindering diffusion of biocide) and thus would be more susceptible to the biocidal effects of hydrogen peroxide.

The results of the treatments with the biocide solutions are shown in FIGS. 1–4 of the accompanying drawings. In the graphs presented, the CFU data were normalised with respect to the discs which were exposed to zero concentrations of the biocide.

FIG. 1 is a plot of hydrogen peroxide concentration vs. percentage surviving fraction of microorganisms (both total and attached). The control biofilms established on the Trylon discs i.e. without catalyst were unaffected by the concentration of hydrogen peroxide employed. In contrast both the total and attached populations were substantially reduced on the copper and cobalt containing discs. As can be seen from the graphs cobalt was significantly better in its enhancement of bacterial kill than copper.

Figure 2:
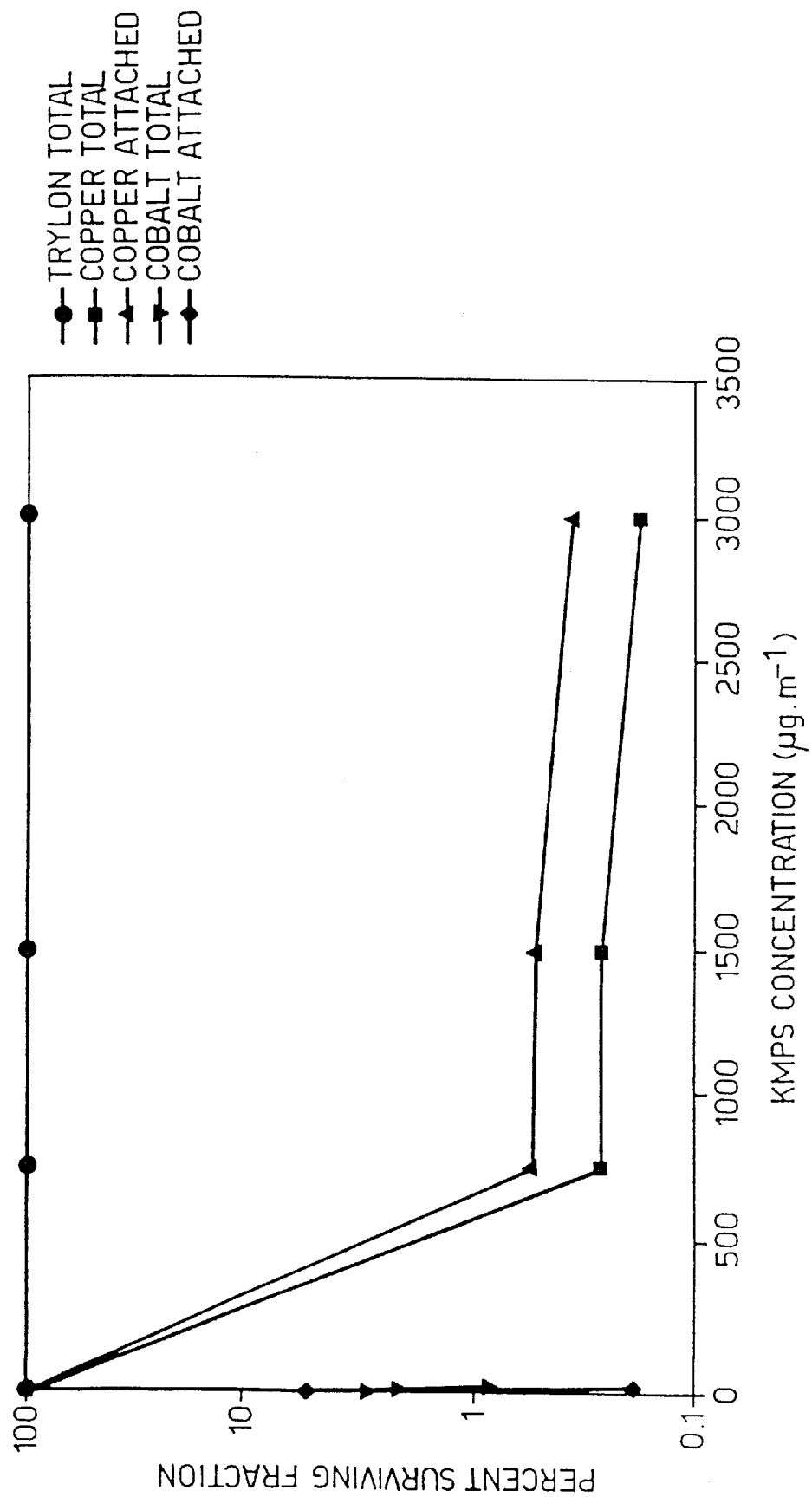
FIG. 2 is a plot of potassium monopersulfate (KMPS) concentration vs. percentage surviving fraction of microorganisms (both total and attached).

FIG. 2 is a plot of KMPS concentration vs. percentage surviving fraction of microorganisms (both total and attached). The control biofilms established on the Trylon discs i.e. without catalyst were unaffected by the concentration of KMPS employed. In contrast both the total and attached populations were substantially reduced on the copper and cobalt containing discs. As can be seen from the graphs cobalt was particularly effective in enhancing bacterial kill at very low concentrations of KMPS.

Figure 3:
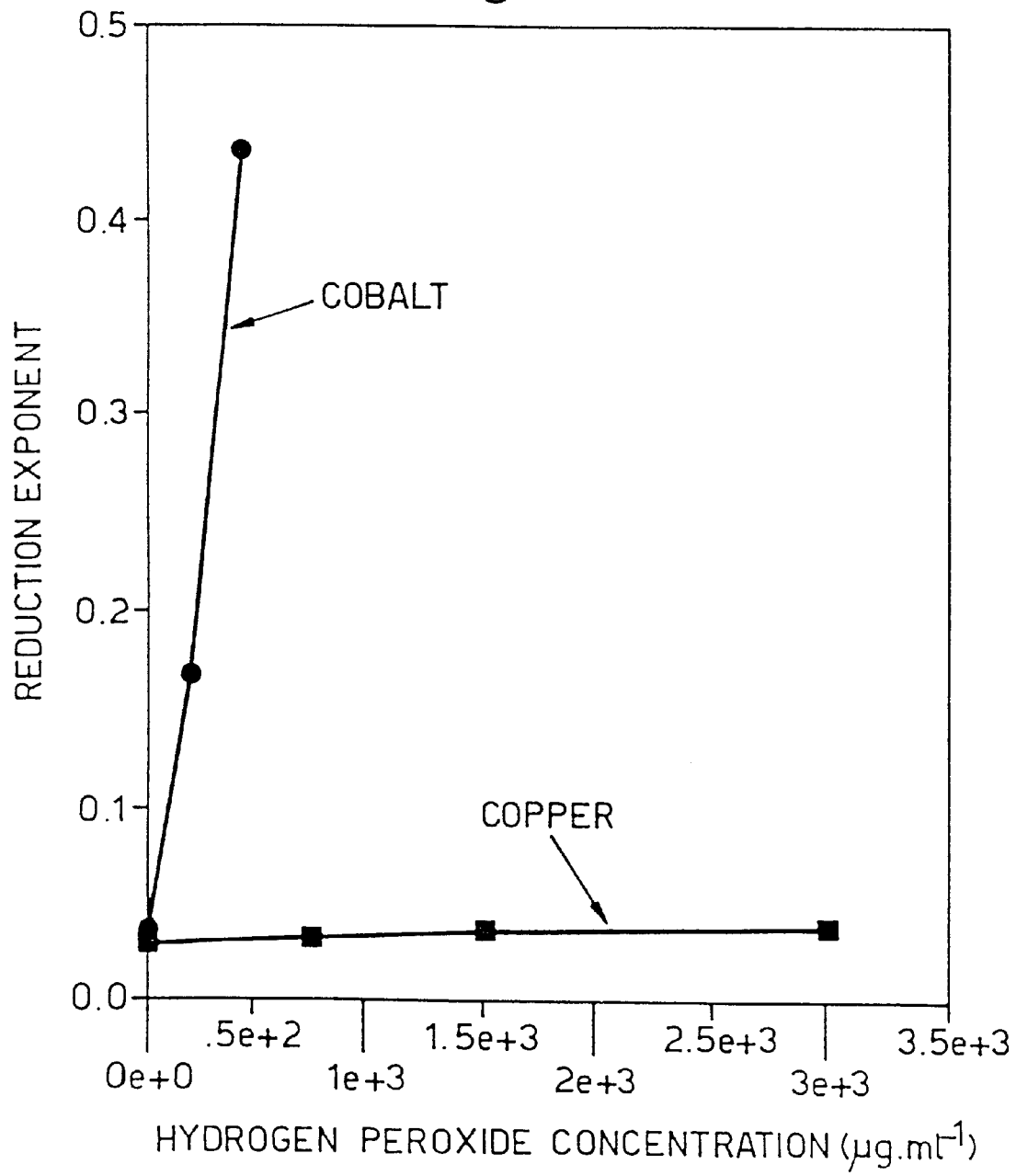
FIG. 3 is a graph demonstrating the effect of hydrogen peroxide on the reduction exponent k.
Figure 4:
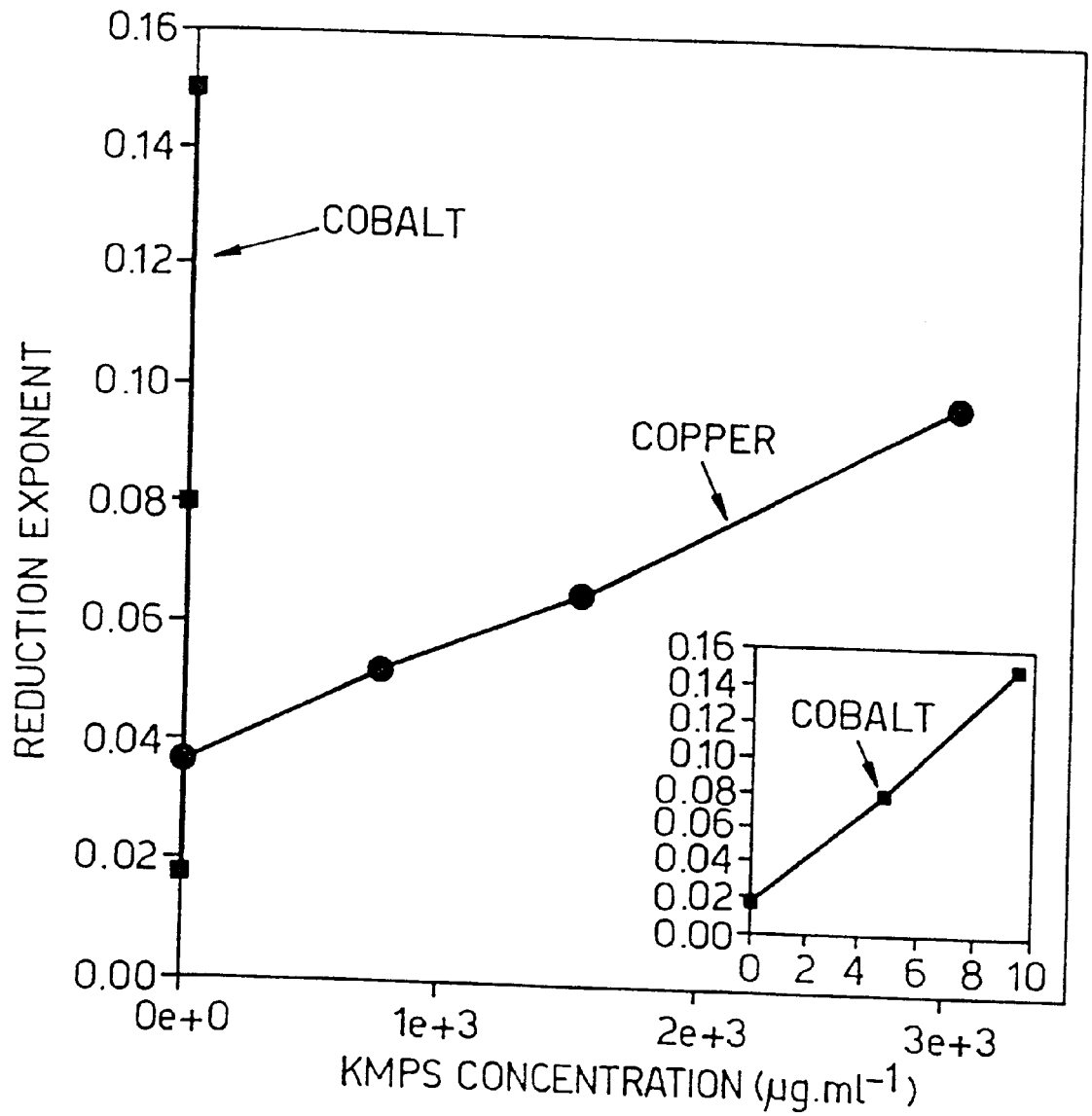
FIG. 4 is a graph demonstrating the effect of KMPS on the reduction exponent k.

FIG. 3 is graph demonstrating the effect of hydrogen peroxide on the reduction exponent k. FIG. 4 is similar but shows the results for KMPS. These graphs clearly demonstrate that the microorganisms which survived the disinfectant tratment were less firmly attached after treatment on a catalyst containing material and would therefore be more easily removed by normal cleaning procedures. The attached survivors became more readily removed with increasing biocide concentrations.

We claim:

1. A process for the disinfection of a surface with a hygiene agent which comprises the steps of:
    a) providing at the surface a non-photochemical catalyst for catalyzing the formation of an hygiene agent from one or more precursors, whereby said catalyst becomes deposited at said surface, and,
    b) subsequently treating the surface with a treatment agent comprising at least one hygiene agent precursor, such that the hygiene agent is generated at and disinfects said surface.

2. A process for the disinfection of a surface having microbial growth thereupon which comprises the step of treating the surface which has a non-photochemical catalyst bound thereto with a treatment agent comprising at least one hygiene agent precursor which forms said treatment agent in the presence of said catalyst.

3. A process for the manufacture of a three-dimensional article which includes the step of incorporating therein, at the time of manufacture, a non-photochemical catalyst capable of transforming at least one hygiene agent precursor into an hygiene agent, wherein the article is such that in use microbial growth will occur on a surface of the article.

4. A process according to claim 1 wherein the hygiene agent and/or the at least one hygiene agent precursor is a peroxy compound, isothiazolone, halide or hypohalite.

5. A process according to claim 1 wherein the hygiene agent and/or the at least one hygiene agent precursor is hydrogen peroxide, sodium peroxide, peracetic acid, performic acid, a monopersulphate salt or an imidoperoxycarboxylic acid.

6. A process according to claim 1 wherein the non-photochemical catalyst is a transition metal or compound thereof.

7. A process according to claim 1 wherein the concentration of the at least one hygiene agent precursor in the treatment agent is at least about 10 ppm.

8. A three-dimensional article having incorporated therein, at the time of manufacture, a non-photochemical catalyst capable of transforming at least one hygiene agent precursor into an hygiene agent effective against microorganisms, wherein the article is such that in use microbial growth will occur on a surface of the article.

9. A process according to claim 1 wherein the concentration of the at least one hygiene agent precursor in the treatment agent is less than about 40% w/v.

10. A method of removing microorganisms from a surface comprising:
    a) providing a surface having a non-photochemical catalyst associated therewith;
    b) placing the surface in an environment that leads to microorganism growth on at least a portion of the surface; and
    c) contacting at least a portion of the surface with a hygiene agent precursor such that a hygiene agent is generated by catalysis at the surface.

11. The method according to claim 10 wherein the step of contacting the surface with the hygiene agent precursor occurs when the surface is in the same location as when the surface was in the environment leading to microorganism growth.

* * * * *